US010524534B2

(12) United States Patent
Smith

(10) Patent No.: US 10,524,534 B2
(45) Date of Patent: Jan. 7, 2020

(54) CASTLESS STANCE CORRECTED PROSTETIC AND METHOD OF FORMING SAME

(71) Applicant: VERTICAL FOOT ALIGNMENT SYSTEMS PTY LIMITED, Marrickville, New South Wales (AU)

(72) Inventor: Neil Robert Smith, Marrickville (AU)

(73) Assignee: VFAS INTERNATIONAL HOLDINGS PTY LIMITED, New South Wales (AU)

( * ) Notice: Subject to any disclaimer, the term of this patent is extended or adjusted under 35 U.S.C. 154(b) by 695 days.

(21) Appl. No.: 15/512,077

(22) PCT Filed: Sep. 19, 2014

(86) PCT No.: PCT/AU2014/050242
§ 371 (c)(1),
(2) Date: Mar. 17, 2017

(87) PCT Pub. No.: WO2015/039191
PCT Pub. Date: Mar. 26, 2015

(65) Prior Publication Data
US 2017/0273397 A1 Sep. 28, 2017

(30) Foreign Application Priority Data
Sep. 20, 2013 (AU) ................................ 2013903637

(51) Int. Cl.
*A43B 17/00* (2006.01)
*A43B 7/24* (2006.01)
(Continued)

(52) U.S. Cl.
CPC ................ *A43B 7/24* (2013.01); *A43B 7/141* (2013.01); *A43B 7/142* (2013.01); *A43B 7/143* (2013.01);
(Continued)

(58) Field of Classification Search
CPC .... A43B 13/386; A43B 17/006; A43B 17/003
(Continued)

(56) References Cited

U.S. PATENT DOCUMENTS 3,591,882 A * 7/1971 Pearsall ................ A43D 35/00
12/146 B
3,895,405 A * 7/1975 Edwards ................. A43B 7/28
12/146 M (Continued)

FOREIGN PATENT DOCUMENTS

WO WO-2007/018449 A2 2/2007
WO WO-2012/103521 A1 8/2012

*Primary Examiner* — Marie D Bays
(74) *Attorney, Agent, or Firm* — Polsinelli PC

(57) ABSTRACT

A method of forming a castless orthotic for a patient's foot in need thereof. The method comprises preparing an orthotic template for the foot wherein the template extends between a heel end and a toe end. In preparing the template the steps of attaching a three-quarter length or full length upper thermoplastic material to a or three-quarter length lower thermoplastic material, or providing a thermoplastic material having a variable thickness such that said thickness decreases from said heel end to said toe end is provided. Then attaching an outer lower layer to the lower thermoplastic material and attaching an outer upper layer to the upper thermoplastic material, or attaching an outer layer to each face of the variable thickness thermoplastic material and heating the prepared orthotic template for a predetermined period of time at a predetermined temperature to soften the orthotic template. A wrap is then placed on top of the foot foam and the foot of the patient is placed on top of the wrap and foot foam. The patient's foot is lifted and the heated orthotic template is placed on top of the wrap and then placing the patient's foot on top of the heated orthotic template. The wrap is placed about the longitudinal axis of the foot to retain the heated orthotic template intermediate (Continued)

the sole of the foot and the foot foam whereby the sides of the orthotic template are particularly supported by the wrap. The method further includes ensuring the foot is positioned over a cuboid support and a medial longitudinal arch support wherein the cuboid support is disposed on the outside of the bottom of the foot and the cuboid support is moved to push the foot upwardly until a resistance is felt, and where the foot is also positioned over the medial longitudinal arch support which is then pushed and pulled upwardly until the foot is moved into a neutral position or if it is unable to be translated or rotated due to until it reaches its end range of motion. At this time, the heel of the patient's foot is lifted to place their weight substantially on the front of their foot and a coolant is applied to at least the heel end of the orthotic template.

24 Claims, 26 Drawing Sheets

(51) Int. Cl.

| | |
|---|---|
| ***A43B 13/38*** | (2006.01) |
| ***A43B 7/28*** | (2006.01) |
| ***A61F 5/14*** | (2006.01) |
| ***B29C 51/28*** | (2006.01) |
| ***A43B 7/14*** | (2006.01) |
| ***A43B 17/03*** | (2006.01) |
| ***A43B 17/14*** | (2006.01) |
| ***A43D 1/02*** | (2006.01) |
| ***A61F 5/01*** | (2006.01) |

(52) U.S. Cl.
CPC .............. *A43B 7/144* (2013.01); *A43B 7/149* (2013.01); *A43B 7/1465* (2013.01); *A43B 7/28* (2013.01); *A43B 13/386* (2013.01); *A43B 17/003* (2013.01); *A43B 17/006* (2013.01); *A43B 17/035* (2013.01); *A43B 17/14* (2013.01); *A43D 1/022* (2013.01); *A61F 5/0111* (2013.01); *A61F 5/14* (2013.01); *B29C 51/28* (2013.01)

(58) Field of Classification Search
USPC .............................................................. 36/44
See application file for complete search history.

(56) References Cited

U.S. PATENT DOCUMENTS

| | | | | |
|---|---|---|---|---|
| 4,133,118 A * | 1/1979 | Khalsa | A43B 7/14 | 36/29 |
| 4,296,053 A * | 10/1981 | Doerer | B29C 44/14 | 264/421 |
| 4,338,734 A * | 7/1982 | Schwartz | A43B 7/141 | 36/44 |
| 4,716,662 A * | 1/1988 | Bar | A43B 7/28 | 12/146 B |
| 5,123,180 A * | 6/1992 | Nannig | A43B 7/141 | 36/43 |
| 5,733,647 A * | 3/1998 | Moore, III | A43B 7/144 | 36/43 |
| 6,195,917 B1 * | 3/2001 | Dieckhaus | A43B 7/141 | 36/154 |
| 6,210,788 B1 * | 4/2001 | Cuypers | C08J 9/32 | 156/78 |
| 6,346,210 B1 * | 2/2002 | Swartz | A43B 3/28 | 264/320 |
| 6,560,902 B1 * | 5/2003 | Eschweiler | A43B 7/141 | 36/44 |
| 7,657,054 B2 | 2/2010 | Phillips | | |
| 7,752,773 B2 * | 7/2010 | McCarron | A43B 3/0078 | 36/140 |
| 9,565,888 B2 * | 2/2017 | Joseph | A43B 1/0027 | |
| 2002/0043005 A1 * | 4/2002 | Blackburn | A43B 17/02 | 36/44 |
| 2002/0050080 A1 * | 5/2002 | Vasyli | A43B 7/141 | 36/145 |
| 2003/0009915 A1 * | 1/2003 | Bacon | A43B 7/142 | 36/44 |
| 2003/0061735 A1 * | 4/2003 | Polifroni | A43B 7/141 | 36/44 |
| 2003/0061736 A1 * | 4/2003 | Polifroni | A43B 7/14 | 36/44 |
| 2007/0234592 A1 * | 10/2007 | Crates | A43B 1/0045 | 36/44 |
| 2007/0277397 A1 * | 12/2007 | Chen | A43B 7/141 | 36/44 |
| 2007/0289170 A1 * | 12/2007 | Avent | A61F 5/14 | 36/166 |
| 2008/0010856 A1 | 1/2008 | Hakkala | | |
| 2011/0307081 A1 | 12/2011 | McDuff | | |
| 2012/0090198 A1 * | 4/2012 | Stratten | A43B 1/0045 | 36/44 |
| 2012/0204444 A1 * | 8/2012 | Liu | A43B 1/0045 | 36/44 |

* cited by examiner

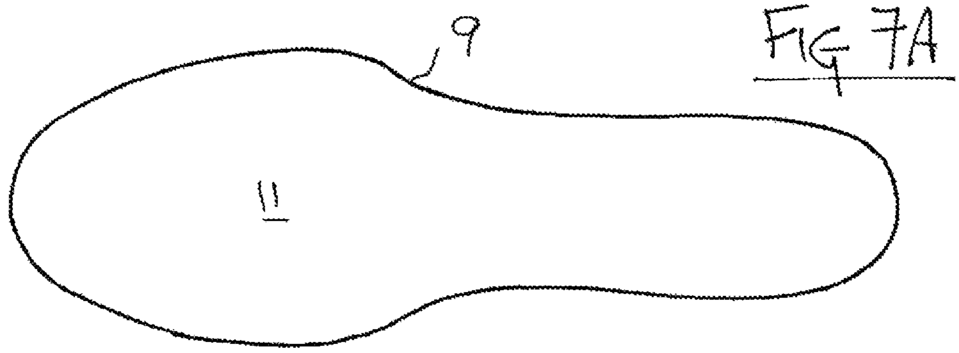
Fig. 7A
Fig. 7B
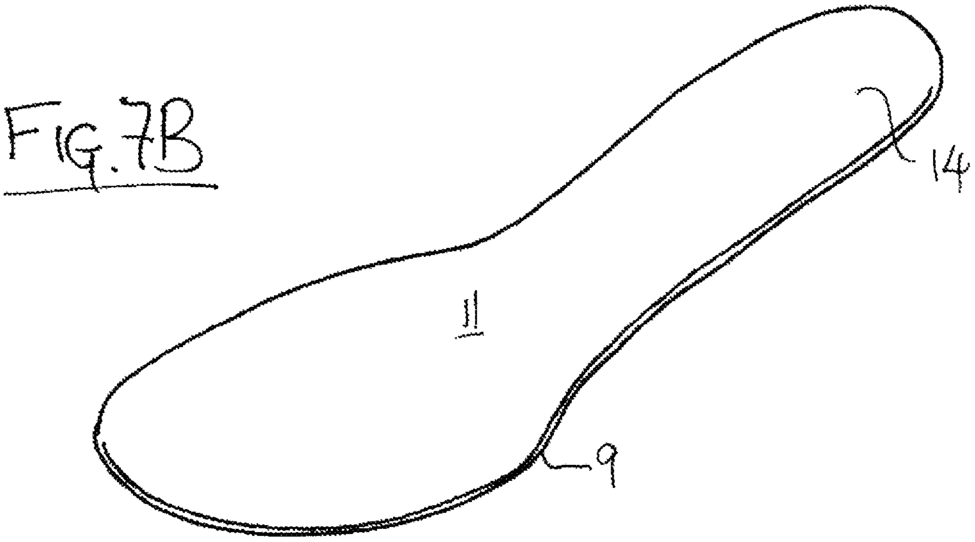
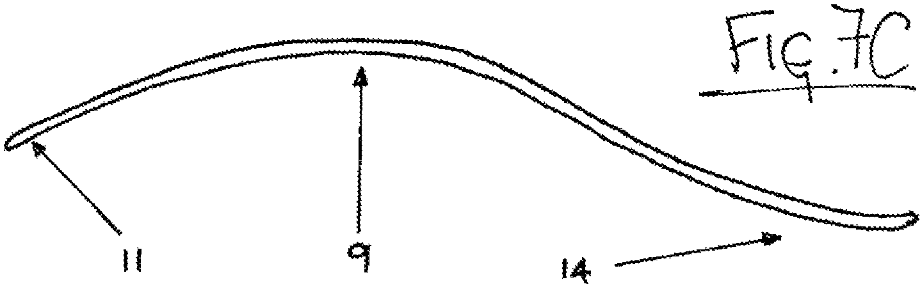
Fig. 7C

CASTLESS STANCE CORRECTED PROSTETIC AND METHOD OF FORMING SAME

CROSS REFERENCE TO RELATED APPLICATIONS

This application is a National Phase filing under 35 U.S.C. § 371 of PCT/AU2014/050242 filed on Sep. 19, 2014. The entire contents of this application are hereby incorporated by reference.

FIELD OF THE INVENTION

The present invention relates to orthotics for the feet, also known as innersoles, which are generally planar shaped supports that are correctively shaped and which are worn inside shoes functioning to correct defects in the stance of the user or patient.

BACKGROUND ART

The traditional methods of making such orthotics involve the taking of a plaster cast of the patient's foot such as set out in U.S. Pat. No. 7,125,509 to the present inventor, which exemplify this art. Once the plaster cast has been made, a replica of the underside of the foot is fabricated and the final plaster orthotic is moulded onto that replica.

In particular, the abovementioned patent describes how the stance of the patient's foot can be corrected whilst the patient is bearing his or her own weight so as to correct inherent defects and thereby ensure that the cast is taken whilst the patient's foot is in the corrected position. This is because the foot alignment is physically manipulated from which position an orthotic for a corrected stance is advantageously provided.

It is also known to create an orthotic mould directly from the patient's foot with the moulding process being conducted whilst the patient is either lying down or sitting down. In either of these two positions no effort is made to correct the stance defects of the patient. Thus the practitioner is required to make an educated guess or apply some other method of determining how the orthotics should be further shaped so as to overcome any stance defects of the patient.

A recently developed method for producing a foot orthotic involves the use of either a pressure sensitive standing platform that typically takes the form of a deformable or pressure-sensitive mat having very many spaced sensors disposed in a two-dimensional array below the surface of or under the mat. With a patient standing on the mat, a map of the pressure exerted by the surface of the foot is provided. This image is then utilised to produce a three-dimensional model purporting to capture the shape of the foot and this image is then manipulated to attempt to account for a preferred shape or pressure map which would be corrective once the foot is bearing weight. This model can then be used to manufacture an orthotic by various means.

Whilst orthotics made by this method may provide some correction to a patient, they can only estimate the necessary corrective function. This is because the orthotic is formed from an image obtained by the patient standing on the mat without re-alignment to a corrected position. As such, the model is not obtained from a foot where force has actually been applied to realign it and place it into a more functional position and change the stresses placed on the foot due to misalignment. The use of 3-D laser scanning in place of pressure sensors has also become known. However, this method suffers the same defect as using pressure sensors. In each case, the apparatus required is relatively expensive.

Genesis of the Invention

The genesis of the present invention is a desire to provide a castless stance corrected prosthetic and method of forming same which enables the orthotic to be moulded directly from the patient's foot whilst the stance of the patient is corrected.

SUMMARY OF THE INVENTION

According to a first aspect of the invention there is provided a method of forming a castless orthotic for a patient's foot in need thereof, the method comprising the steps of:

- preparing an orthotic template for the foot wherein the template extends between a heel end and a toe end, preparing the template including the steps of:
  - attaching a three-quarter length or full length upper thermoplastic material to a or three-quarter length lower thermoplastic material, or providing a thermoplastic material having a variable thickness such that said thickness decreases from said heel end to said toe end;
  - attaching an outer lower layer to the lower thermoplastic material and attaching an outer upper layer to the upper thermoplastic material, or attaching an outer layer to each face of the variable thickness thermoplastic material;
  - heating the prepared orthotic template for a predetermined period of time at a predetermined temperature to soften the orthotic template;
- placing a wrap on top of the foot foam;
- placing the foot of the patient on top of the wrap and foot foam;
- lifting the patient's foot and placing the heated orthotic template on top of the the wrap and then placing the patient's foot on top of the heated orthotic template;
- placing the wrap about the longitudinal axis of the foot to retain the heated orthotic template intermediate the sole of the foot and the foot foam whereby the sides of the orthotic template are particularly supported by the wrap;
- ensuring the foot is positioned over a cuboid support and a medial longitudinal arch support wherein the cuboid support is disposed on the outside of the bottom of the foot and the cuboid support is moved to push the foot upwardly until a resistance is felt, and where the foot is also positioned over the medial longitudinal arch support which is then pushed and pulled upwardly until the foot is moved into a neutral position or if it is unable to be translated or rotated due to until it reaches its end range of motion;
- lifting the heel of the patient's foot to place their weight substantially on the front of their foot;
- applying a coolant to at least the heel end of the orthotic template; and
- if desired, performing slight reshaping of the orthotic template or cooling the entire orthotic.

According to another aspect of the invention there is provided a foot orthotic support arrangement comprising:

- a substantially rigid lower support surface having a plurality of spaced apart inflatable bladders associated therewith, each said bladder being selectively inflatable or deflatable independently of each other said bladder;

an elastically deformable upper foot support adapted to be disposed on said rigid lower support such that at least one bladder is disposed under a medial longitudinal arch of the foot disposed on said upper foot support.

It can therefore be seen that there is advantageously provided a reliable and reproducible method to accurately produce foot orthotics. Further, the apparatus includes foot support elements that have bladders or other actuators integrated to allow 'remote' correction of a foot by means, for example, of a simple valve and air pump. The method and apparatus also allow a faster orthotic production process without compromising accuracy of foot correction. Most advantageously, a patient can walk or otherwise be mobile to practically permit corrections to be made consequently.

BRIEF DESCRIPTION OF THE DRAWINGS

Preferred embodiments of the invention will now be described, by way of example only, with reference to the accompanying drawings in which:

FIGS. 7A-C a top view, a perspective view and a side view respectively of a medial longitudinal arch support for use in making a foot orthotic according to the preferred embodiment;

DETAILED DESCRIPTION

Figure 1:
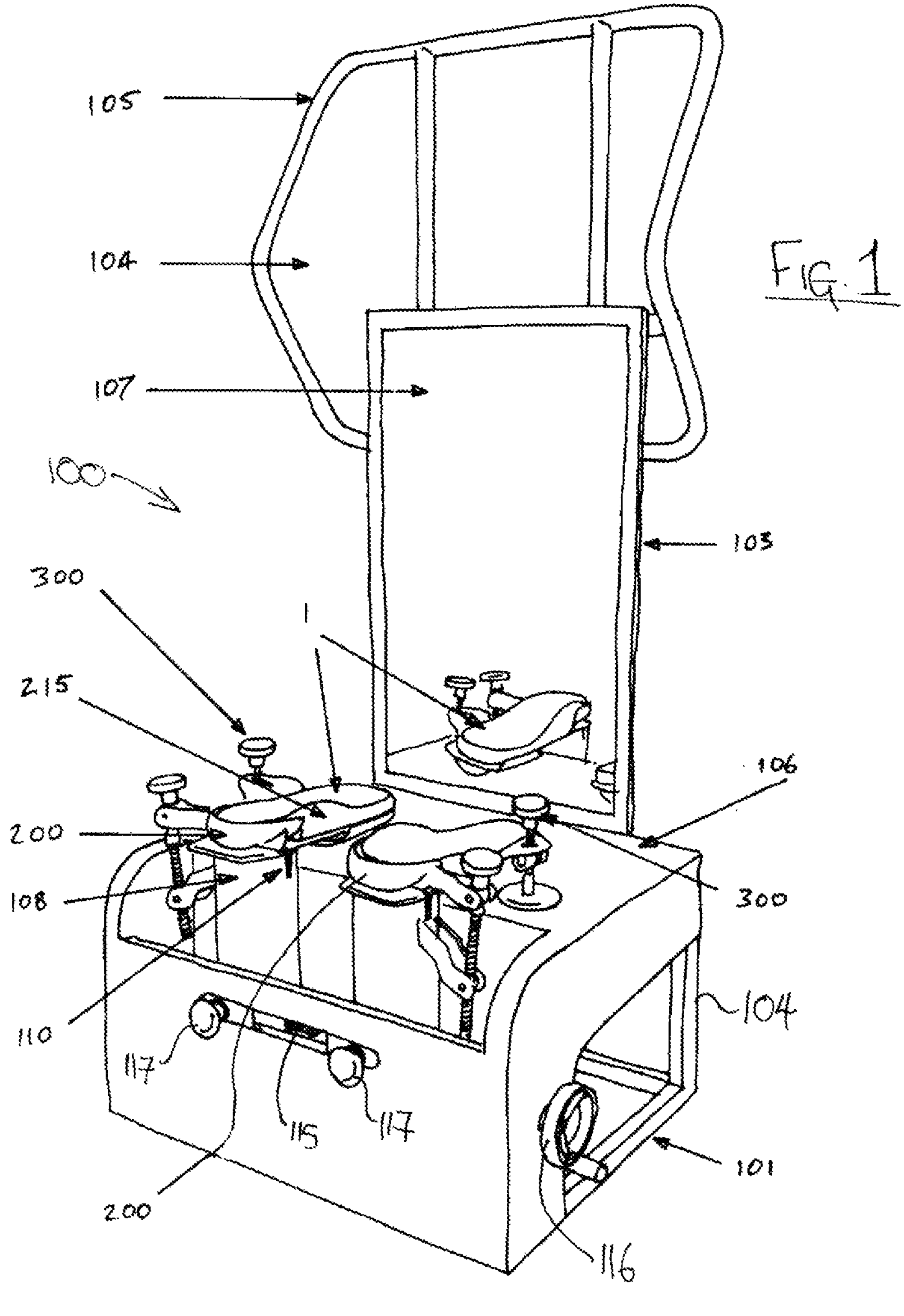
FIG. 1 is a perspective view of a support platform for use in making a foot orthotic according to the preferred embodiment.

In the preferred embodiment, a support platform 100 for use in making a foot orthotic according to the preferred embodiments is shown in FIG. 1. Orthotics are made for a patient's foot with the foot moved into a corrected position. As noted below, the corrected position could be a correctly aligned foot or a foot moved as close to the correctly aligned position as possible.

The standing support platform 100 is provided for a patient to stand on whilst the clinician forms the orthotics 20. Foot foams 1 are supported by fore foot and heel foot supports 300 & 200 as below. The support platform 100 includes a base frame 101 on which horizontal surface 106 is disposed. The frame 101 also supports heel support mechanisms 200 and the surface 106 supports forefoot support mechanisms 300.

The support platform 100 also includes a vertical frame 103 extending a predetermined height above surface 106. At a top end, a handle 104 for patients to grip for stability is provided. Handgrips 105 are disposed on the handle for convenience. Of particular utility, a mirror 107 is mounted across part of the vertical frame 103. This most advantageously allows a practitioner to see the front of a patient's legs when operating from behind the patient and heel supports 200, or from the sides. The alignment of the front of the knee, ankle and foot can clearly be seen by viewing the mirror between the legs.

Each heel support 200 is mounted on independent pillars 108. The pillars 108 are able to be independently moved vertically by means of a threaded adjustment rod (not illustrated) and can be moved towards or away from each other to suit the width and angle of the patient's stance. This is achieved by means of a winding screw to which at least one of the pillars 108 is threadedly engaged. Handle 116 is disposed on the side of the platform 100. Rotation of the handle 116 causes corresponding movement of the pillars toward or away from each other. It will be appreciated that the vertical height adjustment of the pillars 108 is preferred and not essential.

FIG. 1 also shows a knob 117 at the rear of each pillar 108. The knobs 117 are used to fix the orientation of each pillar in the horizontal plane. This allows to the feet of a patient to be moved into a parallel position.

Figure 2:
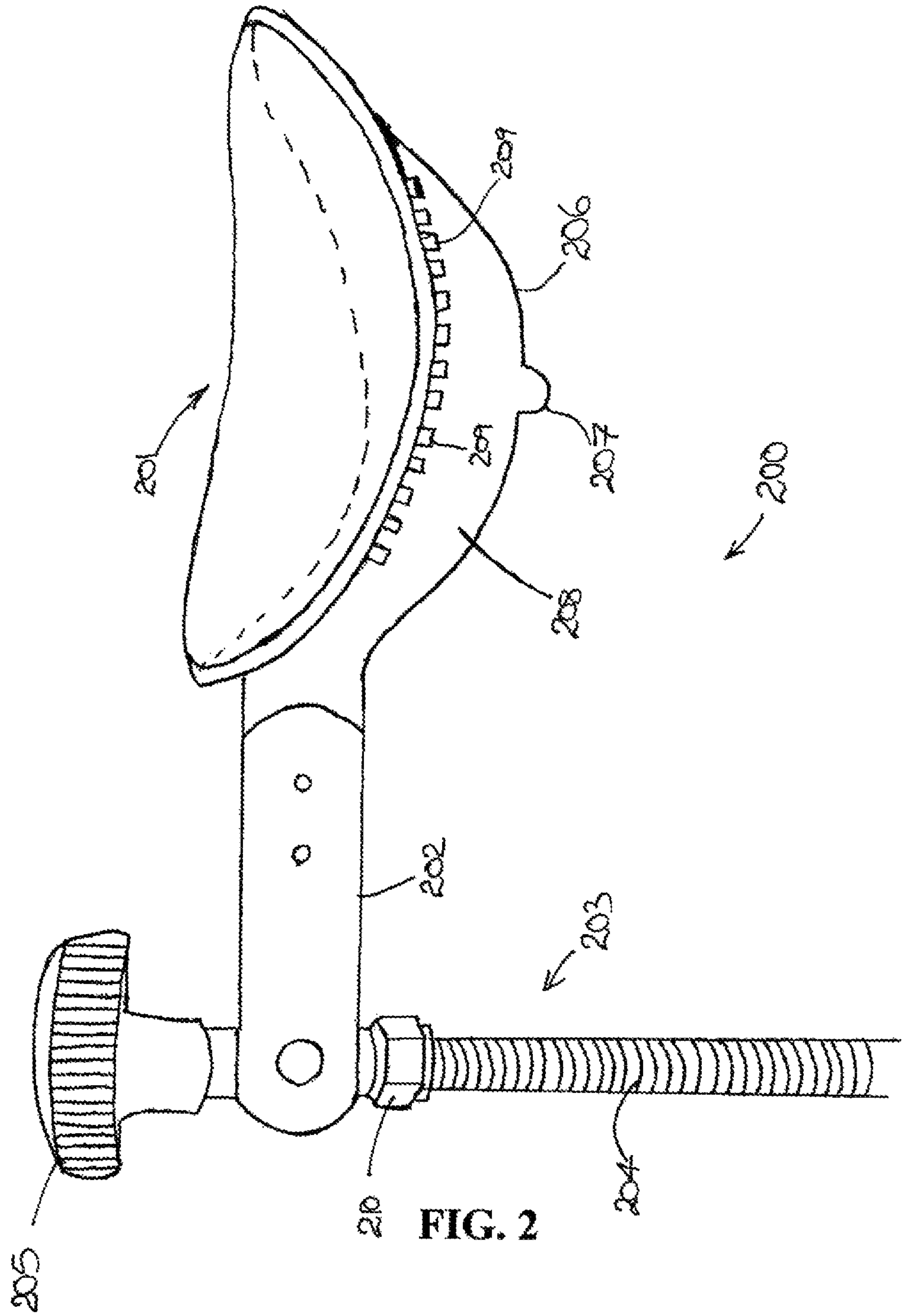
FIG. 2 is a perspective view of the right hand foot heel support of the platform of FIG. 1.

Turning now to FIG. 2, the heel support 200 is shown in more detail. A cupped or otherwise shaped heel supporting surface 201 is mounted to one end of arm 202. The other end of the arm 202 is hingedly mounted to an adjustment post 203. The post 203 includes a nut 210 fixed to the arm 202 and this is threaded to match screw portion 204. A knob 205 at the top of the post 203 moves the thread 204 and causes the nut 210 to move up and down the post 203.

This causes corresponding movement of the heel supporting surface 201. This is engaged with a slot 110 in an upper face of each pillar 108 by means of a curved rib 206. A lower centre projection 207 is also preferably provided. A gear 208 having a plurality of teeth 209 is disposed at the boundary of the supporting surface 201 and the curved rib 206. An outer support 302 is used to support the inside of a foot as required.

In use, the knob 205 is rotated and this causes corresponding rotation of the heel support surface 201 perpendicular to the longitudinal axis of the foot. Not only does the heel support 201 rotate, the engagement with the slot 110 allows it to translate along the slot 110 correspondingly.

Figure 3:
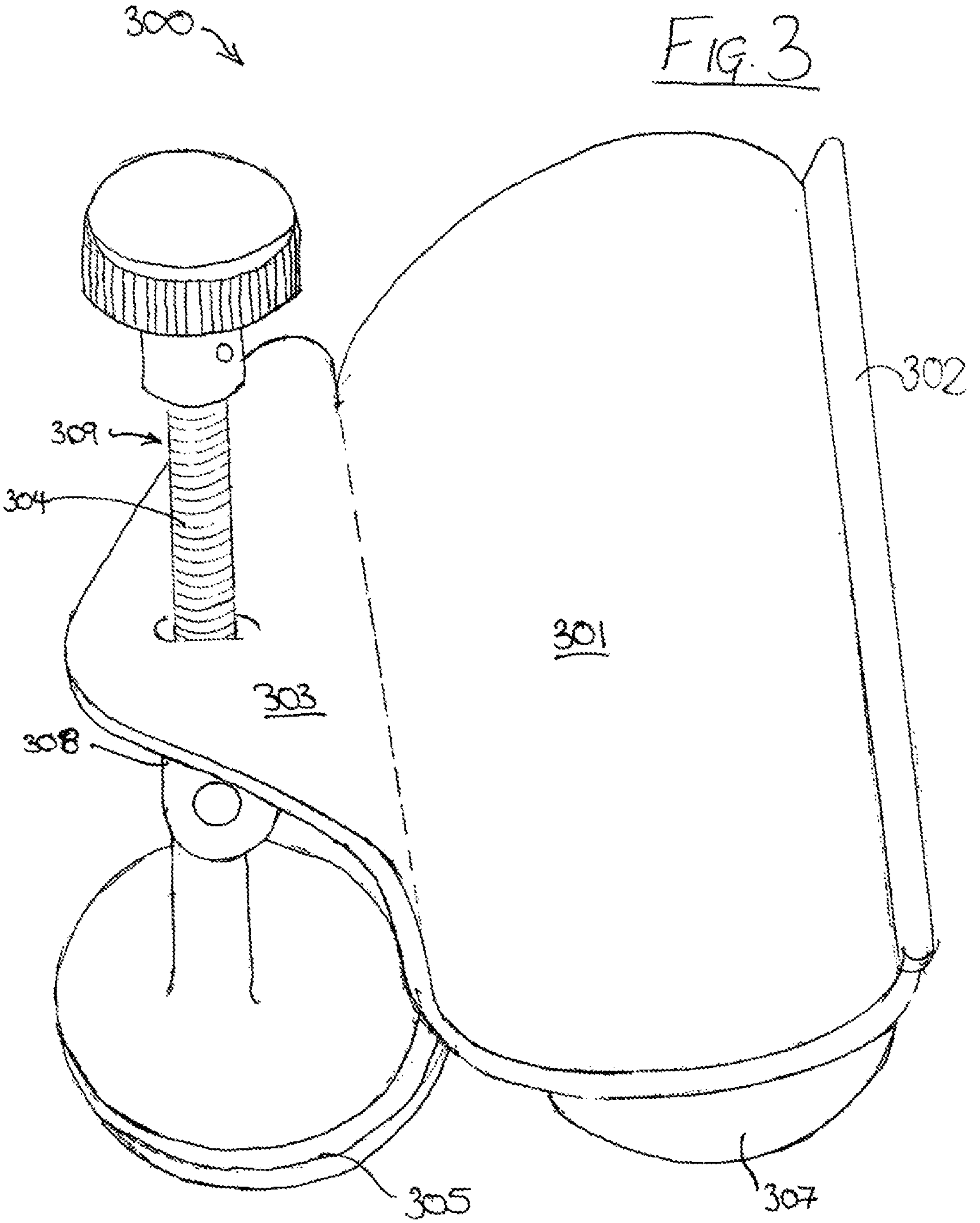
FIG. 3 is a perspective view of the left hand foot front support of the platform of FIG. 1

Referring now to FIG. 3, forefoot support 300 is formed from a supporting platform 301 that is substantially parallel to surface 106. Platform 301 is supported at a lower end by a curved bearing surface 307. This can be formed from a unitary curved projection extending from below surface 301 or formed from sections thereof to provide the same 'rolling' effect.

This rolling effect is provided by arm 303 extending from the platform 301 and being threadedly engaged with adjustment rod 309. A nut 308 is hingedly mounted to a threaded shaft 304. The nut 307 allows the platform 301 to roll along curved bearing surface 307 importantly without moving the platform 301 away from the shaft 304. This is 'anchored' by support foot 305 when under the weight of a patient's foot.

In practice it is found that the desired angle of inward tilt of the surface 301 is between 12° to 18° and most preferably 15°. It will be appreciated that the surfaces 301 need not be able to rotate or tilt, or may be able to rotate outwardly if desired.

It will be appreciated that the patient's stance can be further adjusted by use of a rear foot adjustment curve and/or further adjusting the patient's stance by use of a forefoot adjustment curve. The rear foot and forefoot curves can be those as disclosed in US 2012/015972A1 or labeled 14 and 14' in FIG. 18, the operation of which is described further below.

In this embodiment, a piece of plastic 5 in the form of 2 mm natural polypropylene or similar extends from the heel support 200 to the front support 300 to support the foot foam 1 in place between the heel & front supports 200 & 300 and this acts as support surface 2 for the foot foams 1. The plastic 5 is to support apparatus used to correct the stance of the patient under the load of the patient. The plastic support 5 assists in preventing the foot foams 1 from deforming or collapsing under the weight of the patient.

Figure 4A:
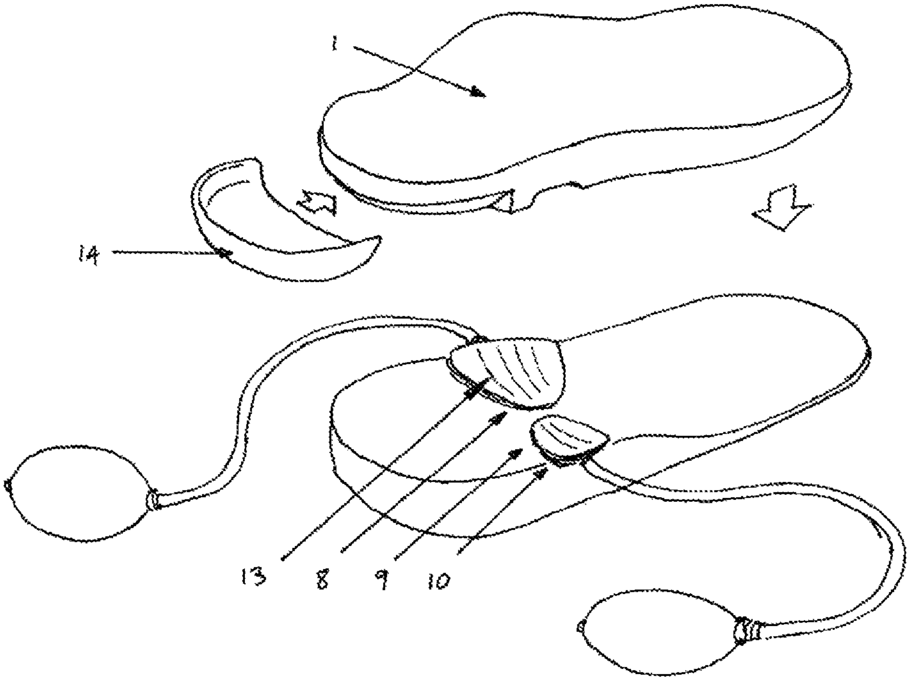
FIGS. 4A & 4B are an exploded and assembled perspective view respectively of an alternative support platform for use in making a foot orthotic according to the preferred embodiment.
Figure 4B:
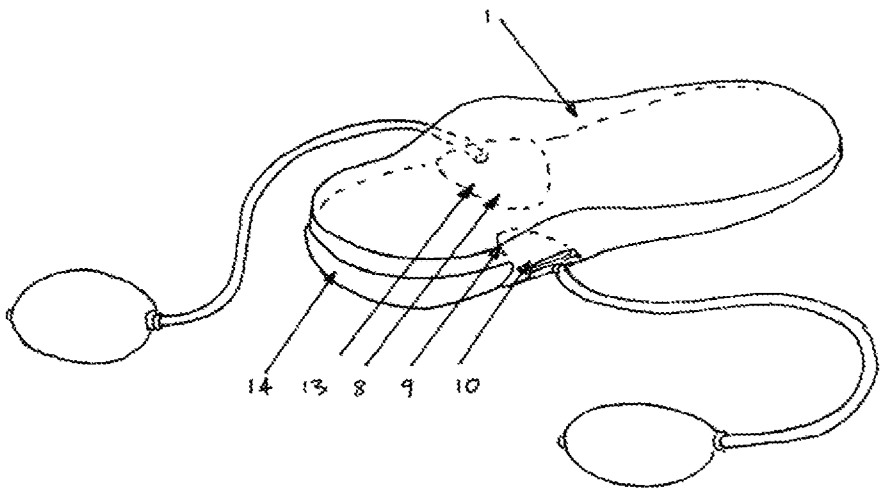
Figure 5:
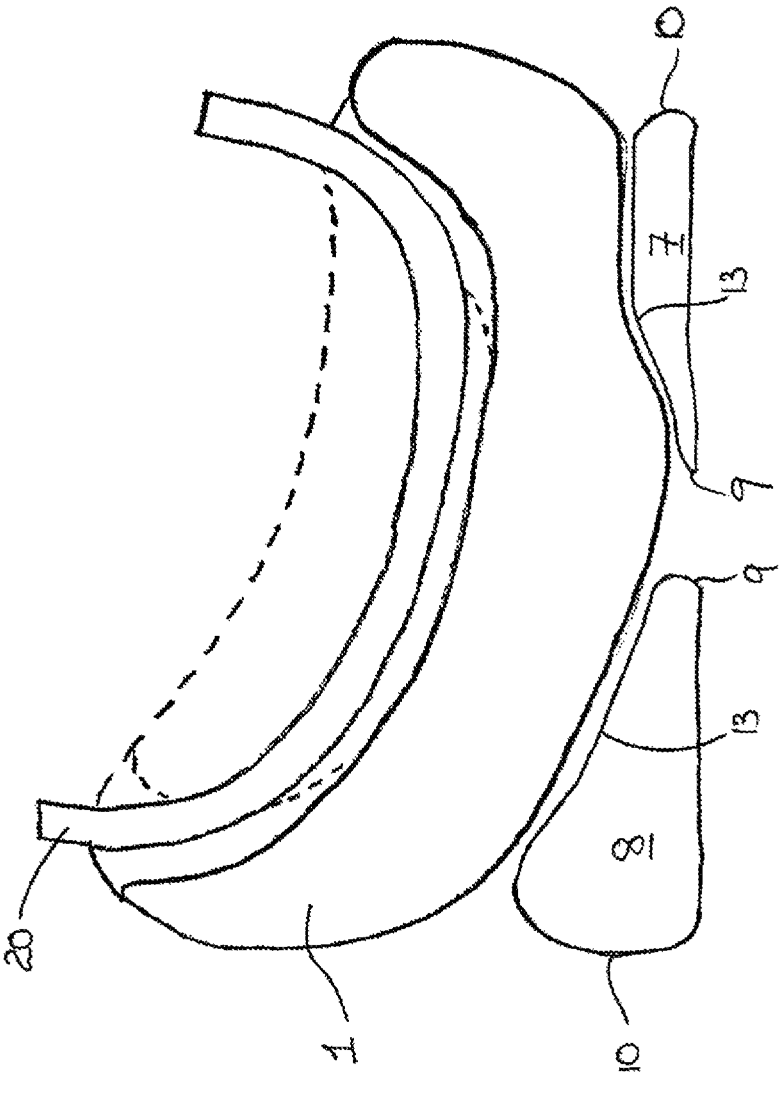
FIG. 5 is a rear view of the support platform of FIG. 4.

It will be appreciated plastic 5 is of no utility in other preferred embodiments such as where using a flat horizontal support surface 6 (as best shown in FIG. 4) including a platform or a table or the floor which adequately supports the foams 1 under the weight of a foot, where the embodiment of FIG. 1 is particularly preferred.

Other preferred embodiments shown in the remaining Figs are similar to FIG. 4 in that the foot foam support 1 is supported by a static flat and non-tiltable platform 6 rather than using the surfaces 200 and 300 of FIG. 1 or 2 that are able to be tilted, etc. Each foot foam support 1 is disposed over a spaced apart pair of bladders 7 & 8. A substantially rigid rear foot curve 14 is disposed under the foot foam 1. This is shown in FIG. 4 and it will be appreciated that the practitioner manipulates the curve 14 to correct the foot. Once moved into a preferred corrected position, the rear foot curve 14 is the 'wedged' to retain the foot with that correction.

Figure 6:
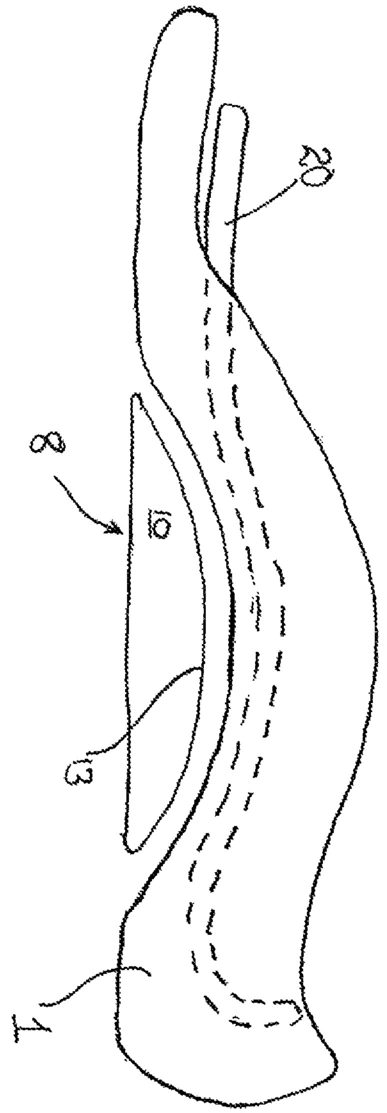
FIG. 6 is a side view of the support platform of FIG. 4.
Figure 18:
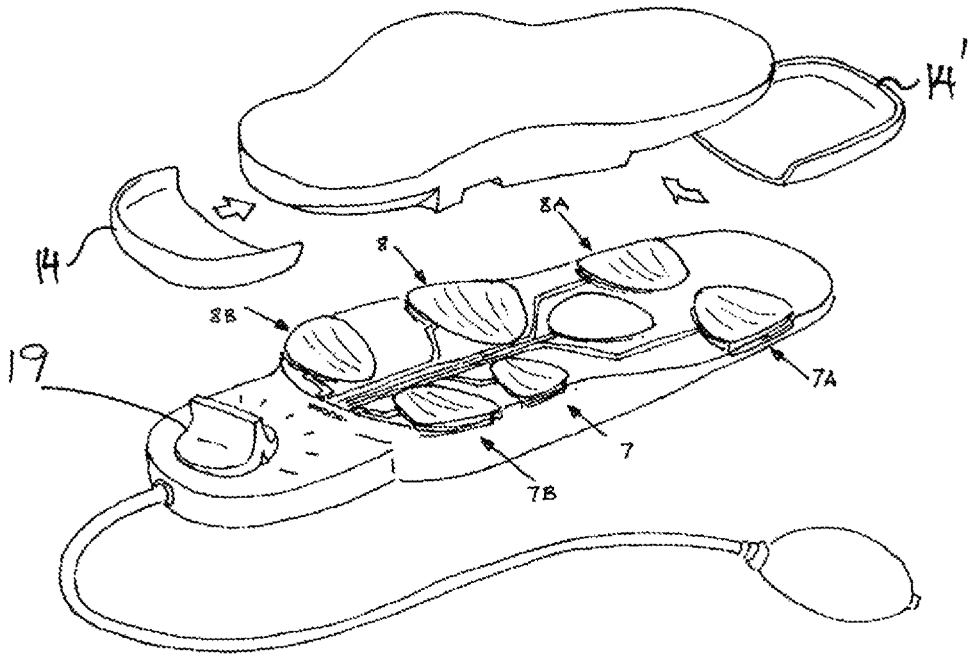
FIGS. 18 & 19 are an exploded and assembled perspective view respectively of alternative support platform to FIG. 4 for use in making a foot orthotic according to the preferred embodiment.

In contrast, FIGS. 6 & 18 shows the case where substantially rigid curve 14 is not employed and movement of the bladders 7B & 8B provide equivalent correction about the heel as the rear foot curve 14. However, once the bladders are suitable inflated, they can be retained in that position so as to hold the foot in that position without using a wedge or the like that is needed when using curve 14 to correct the rear foot position.

It will be appreciated that in the embodiment of FIG. 18, a fore foot curve 14' is also provided and operates in the same manner as the rear foot curve 14 to allow correction to the fore foot whether movable by means of a practitioner's hand, or one or more bladders 7A & 8A.

Each bladder hinges about a front end 9 thereof disposed towards the centre of the foot and the rear end 10 under or protruding from the side of the foot. One bladder 7 is disposed substantially underneath the cuboid on the outside lateral edge of the foot and the other bladder 8 on the inside is disposed substantially underneath the medial longitudinal arch.

Figures 8A, 8B:
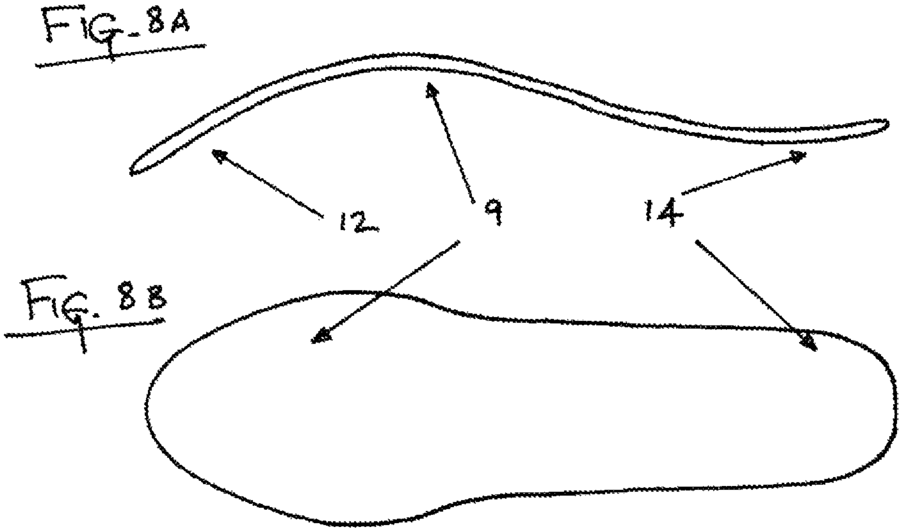
FIGS. 8A & B are a side view and a top view of a cuboid support for use in making a foot orthotic according to the preferred embodiment.

The bladders can be made to allow a medial longitudinal arch (MLA) or cuboid support 11 & 12 (shown in FIGS. 7 & 8) respectively to be disposed on top of or form a leading or upper face 13 of the respective bladders 8 & 7. Movement of the bladders (ie inflation or deflation) causes movement of the foam 1 and the MLA or cuboid supports 11 & 12. This rotates the cuboid or the arch about the longitudinal axis of the foot by lifting and hinging about the front end 9 of the bladders 7 & 8 and correspondingly moving the MLA or cuboid supports 11 & 12 or faces 13 of the bladders when used without supports 11 & 12.

In preferred embodiments, supports 11 & 12 are as shown in FIGS. 7 & 8 in which the supports are not straight levers but are curved so that movement upwards rolls the support a small amount to engage the front 9 as a fulcrum. The cuboid support 11 can have the fulcrum close to its front edge and the MLA support set back therefrom. A conventionally known bulb and air-valve such as used in sphygmomanometers is shown but any air source and valving arrangement can be used.

It will be appreciated that in some preferred embodiments, the MLA and cuboid supports 11 & 12 can be formed as part of the respective bladder 7 & 8 such that the upper face 13 of the bladders 7 & 8 are shaped to perform the function of the MLA and cuboid supports 11 & 12. It will be appreciated that either bladder 7 & 8 can be replaced with an equivalent device capable of moving the foot foam 1 supporting the cuboid or MLA in a like manner. Such devices include a linear actuator or screw device movable upwardly from the platform (or floor if not platform is used), or a mechanical lever such as a hinged MLA or cuboid support, or can be hydraulic, pneumatic, electrically powered or simply manually movable such as by supports shown in FIGS. 7 & 8.

It will be understood in the case of MLA and cuboid supports 11 & 12 being integrally formed with the support surface 13 of a bladder 7 or 8 then the handle portion 14 (seen at 7B, 7C, 8A and 8B in FIG. 6) becomes redundant. Further, the bladders 7 & 8 can be disposed in or integrally formed with the foot foams 1. In this way, the bladders are positioned intrinsically correctly with respect to the foot foams 1.

Figure 13:
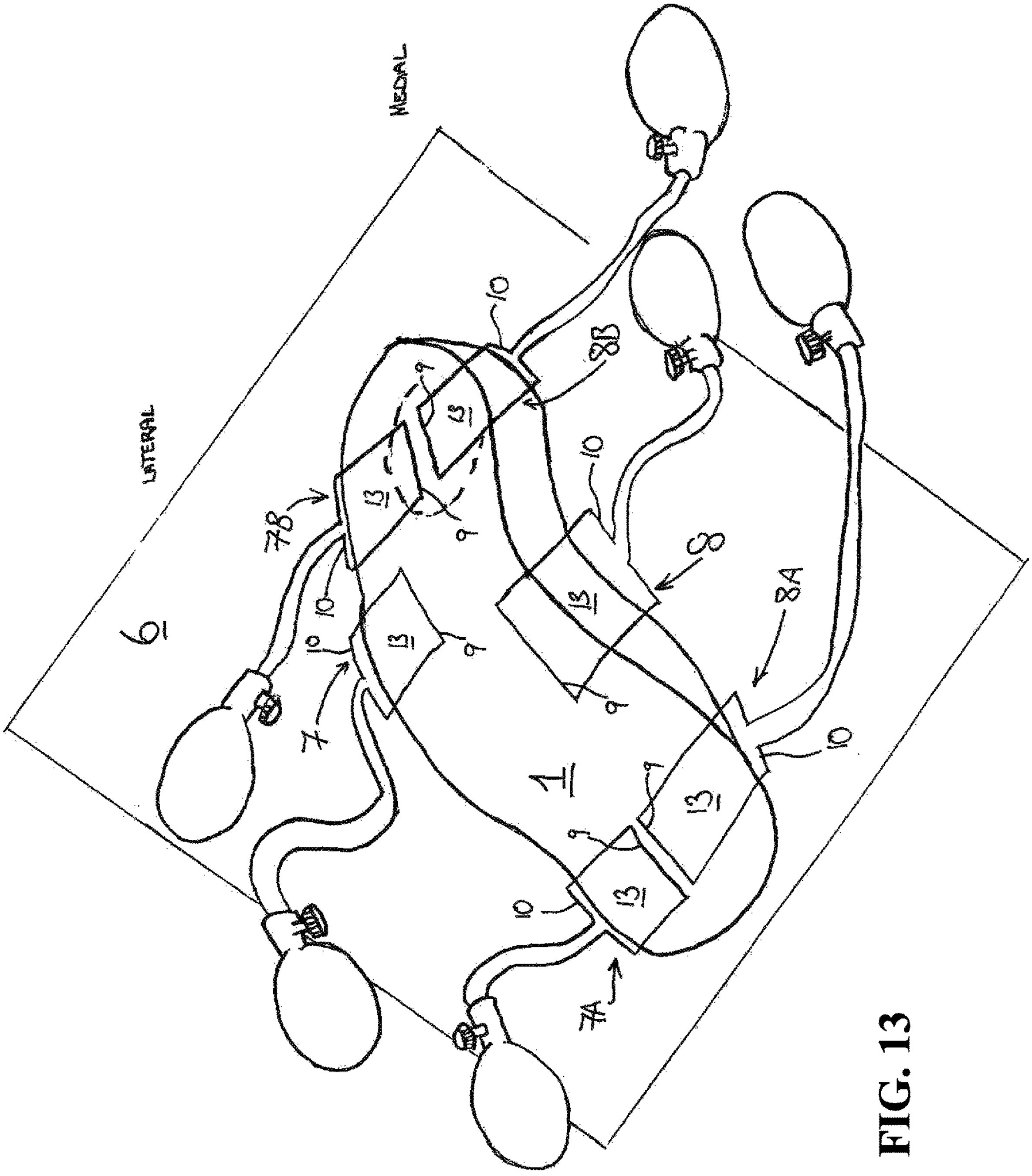
FIG. 13 is a perspective view of an alternative platform for use in making a foot orthotic according to the preferred embodiment.

Referring now to FIG. 13, there is shown another preferred embodiment in which the bladders 7 & 8 are disposed under the MLA and cuboid regions of the foot but there is also provided four other spaced apart bladders 7A, 7B, 8A and 8B, each of which include supports 11A, 11B, 12A and 12B formed on a face thereof, or disposed within. Bladders 7A & 7B are disposed under the outside region of the foot either side of bladder 7 so that bladder 7A is disposed under the foot foam 1 under the ball portion of the foot on an outside and bladder 7B disposed under foam 1 under the heel of the foot on an outside of the foot. Bladders 8A & 8B are disposed correspondingly under the foot foam 1 under the inside portions of the foot either side of bladder 8.

In this embodiment, the use of the support surfaces 200 and 300 as in FIG. 1 can be replaced functionally by the additional bladder arrangement of FIG. 13. The bladders under opposing sides of the foot can be used to counter movement of a bladder on the other side to stabilise the foot where movement of that bladder moves the foot into or towards a corrected or more desired or more neutral position. If necessary, the patient can roll their ankle outwards or inwards to assist in reduction in downward force so that a more neutral position may be obtained.

Once the foot has been moved into the corrected position, and noting this is regardless of the type of platform 106 or 6 used for example, the MLA and cuboid supports 11 & 12 (in FIGS. 7A-7C and 8A-8B) are maintained under the foam 1 so the foot is in a corrected stance. In the case of a bladder 7 or 8 or other device, the device position or bladder inflation is maintained or when manually using the MLA and cuboid supports 11 & 12 of FIGS. 7 & 8, a relatively stiff foam or other temporary support is disposed under the cuboid and arch once the foot is corrected and the supports 11 & 12 removed.

It will be appreciated that in preferred embodiments, a thin preferably plastic sheet layer, for example 0.6 mm thick Promeg®, is disposed under the foam foot supports 1. This is to assist in sliding either the MLA and Cuboid supports or a bladder or similar relocatable device can be slid under the foams 1 without unnecessary resistance.

Figure 9:
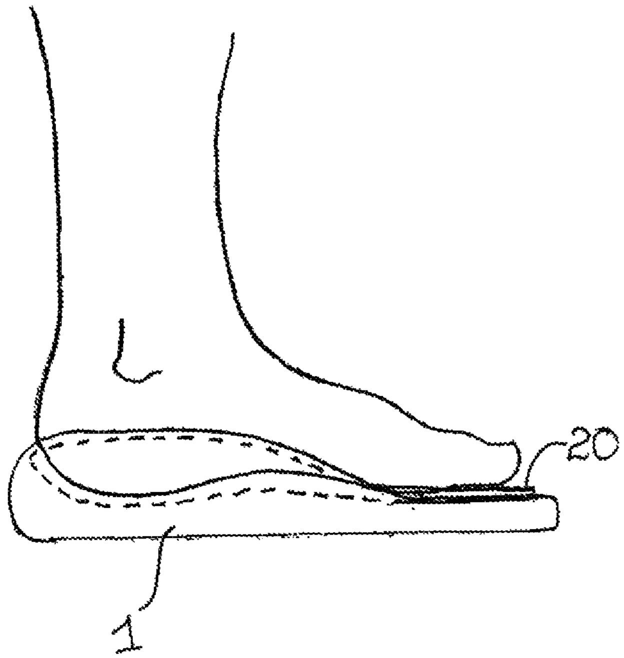
FIG. 9 is a side view of a left foot with a foot orthotic formed according to the preferred embodiment in situ.
Figure 10:
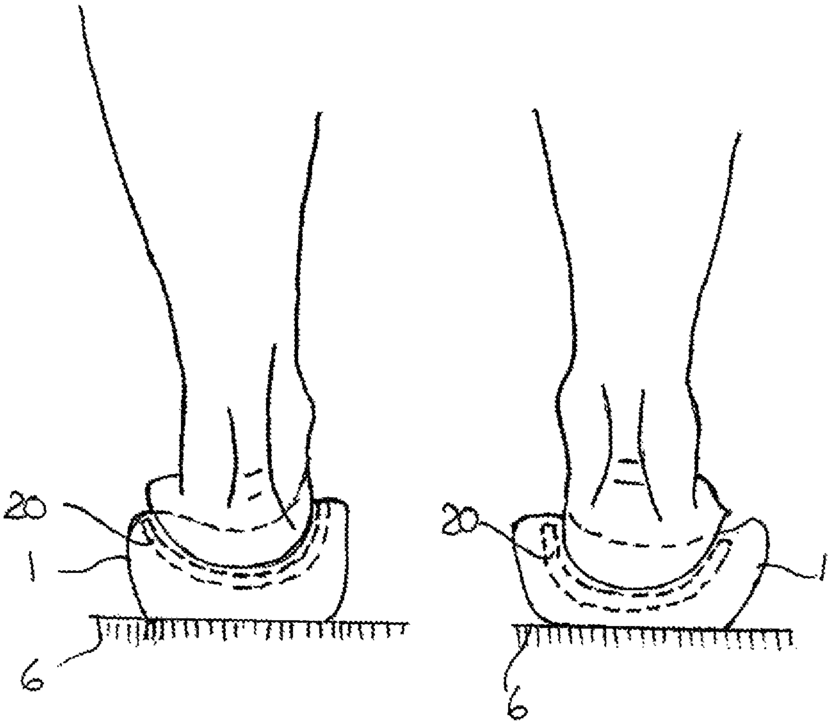
FIG. 10 is an end view of a pair of feet each with a foot orthotic formed according to the preferred embodiment in situ.
Figure 16A:
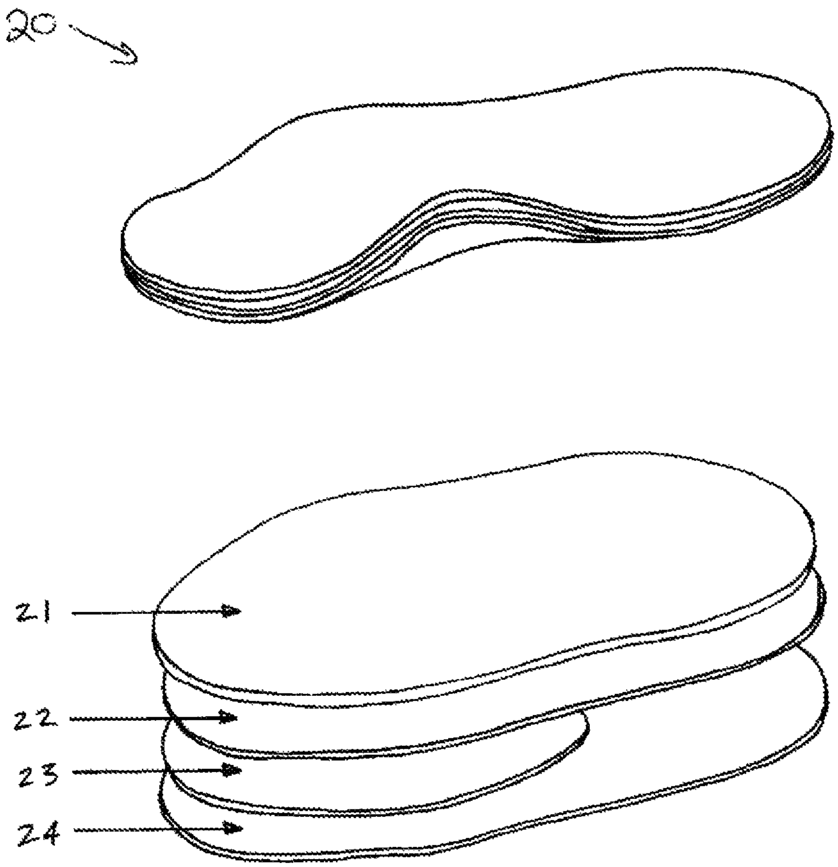
FIGS. 16A to 16C are a perspective view of the corrected orthotic of FIG. 10 and other corrected orthotics according to other preferred embodiments.
Figure 16B:
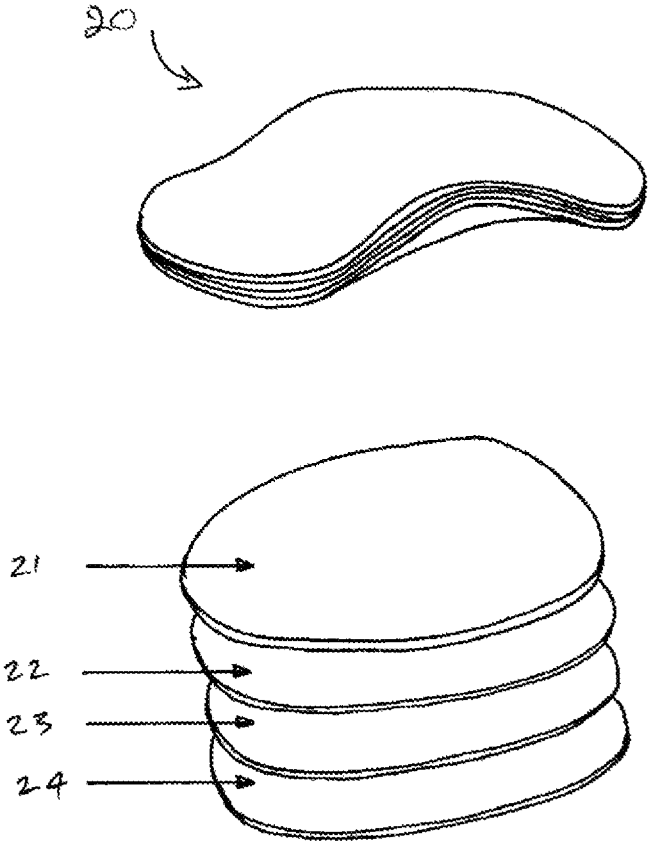
Figure 16C:
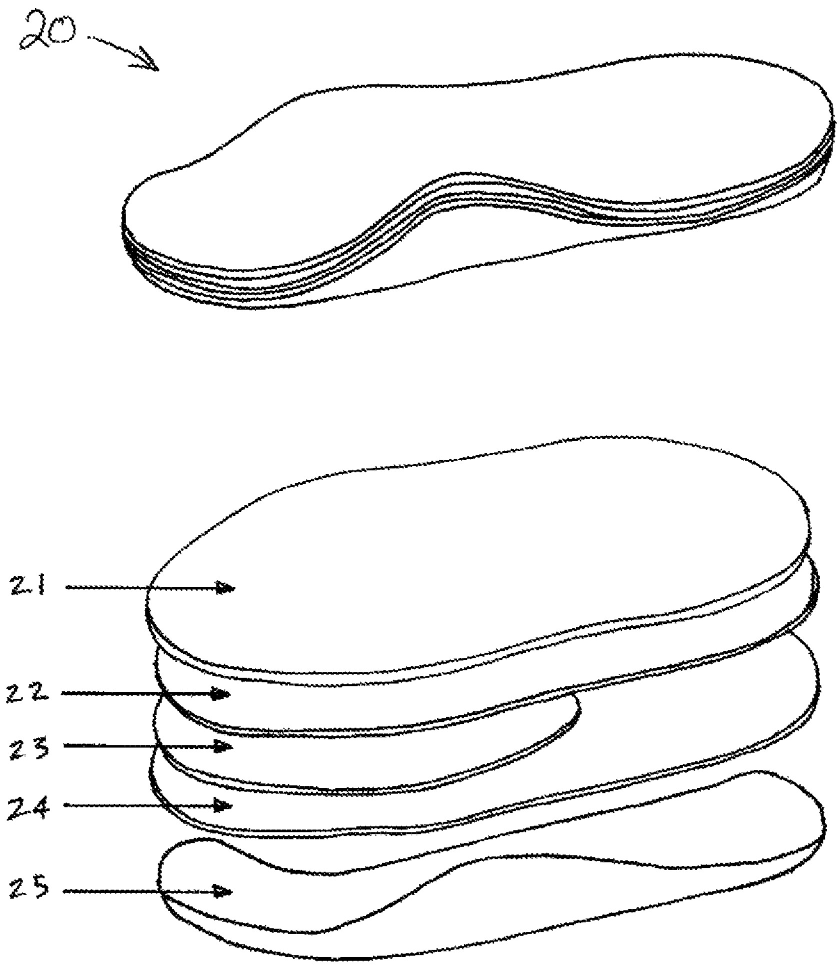

In the process of providing an orthotic for a patient when they are in a corrected stance, orthotics 20 (such as in FIG. 16 showing different preferred embodiments) as templates are prepared by attaching a three-quarter length or full length thermoplastic material (upper) 22 to a three-quarter length thermoplastic material (lower) 23. These are glued or otherwise adhered together. In the preferred embodiments, a polycaprolactone (PCL) or a commercially available product, for example, RELION® is used. Preferred thermoplastic sheet materials are those which are able to be softened at temperatures of the order of 60 C-100 C and are able to be shaped to provide a support for a corrected foot. At room or body temperature, the thermoplastic material is substantially rigid. FIGS. 9 and 10 show the foot of the patient with the orthotic 20 and without correction.

A fabric or other sheet material layer 24 is added over the underside of the full length or three-quarter length thermoplastic material to cover the whole of the full or three-quarter thermoplastic material at the bottom or lower face. The full-length or three-quarter thermoplastic upper material 22 is about 1.4 mm thick and the three-quarter length lower material 23 is about 1.2 mm thick. In the preferred embodiment, the commercially available product CAMBRELLE® lining material forms the bottom or lower layer 24, details of which can be found at http://www.cambrelle.com/Products/. These layers are glued together to form a single piece blank orthotic.

The blank orthotic 20 is placed in an oven at approximately 100° C. for 4 min 30 sec to soften the thermoplastic materials 21 & 22. Other heating methods can be employed as desired, such as microwave ovens or heat guns, for example. The heated blank orthotic 20 is removed from the oven, and has a top foam or cushion layer 21 added. Any preferred material such as leather, vinyl, ethyl vinyl acetate (EVA) and neoprene can be used. This is preferably pre-glued on one side or with the use of a double sided tape. The top layer, in addition to desirably providing a long wearing surface also protects the foot from the heated blank orthotic 20.

It will be appreciated that the template 20 can alternatively be supplied with the top covers already applied requiring that the orthotic heated only from beneath.

The patient is stood on the foot foams 1 where they lift either their left or right foot and the heated blank orthotic 20 is placed onto the foot foam 1 with the top foam or cushion layer 21 added. The heated blank orthotic is then smoothed into the contours of the foot foam 1 to reduce or eliminate any creases forming in the heated blank orthotic 20 as it cools under the load of a foot.

Figure 11:
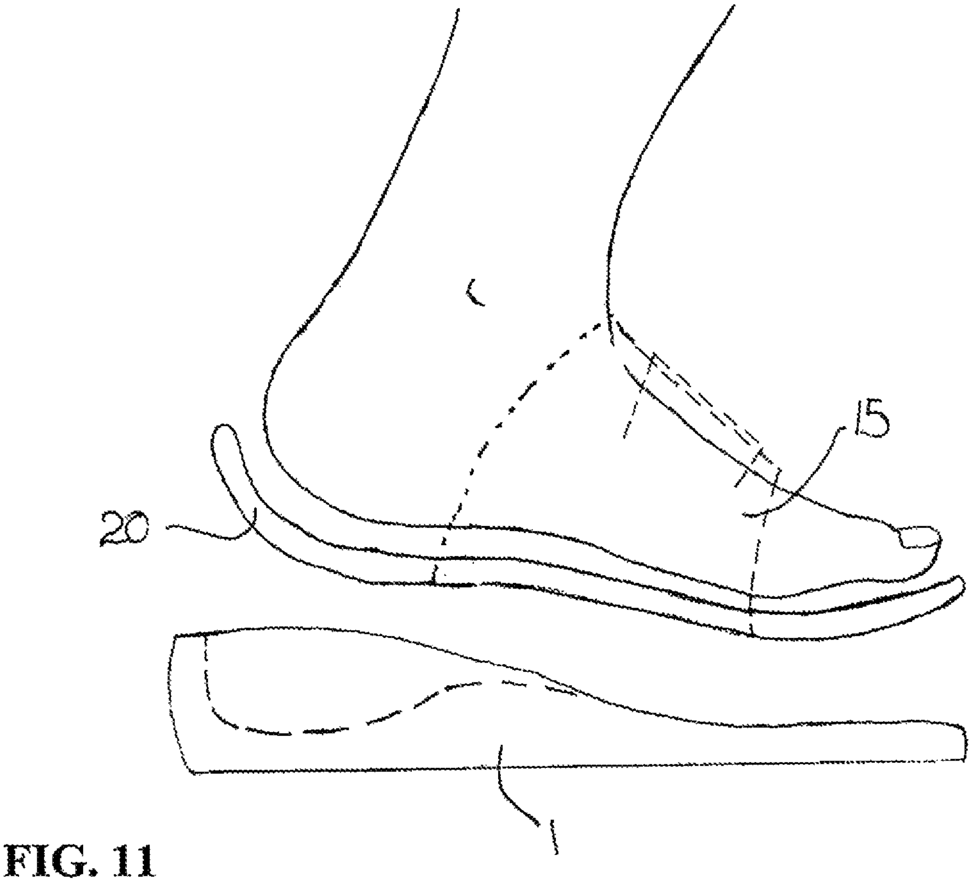
FIG. 11 is an exploded side view of the left hand foot showing a foot wrap.
Figure 12:
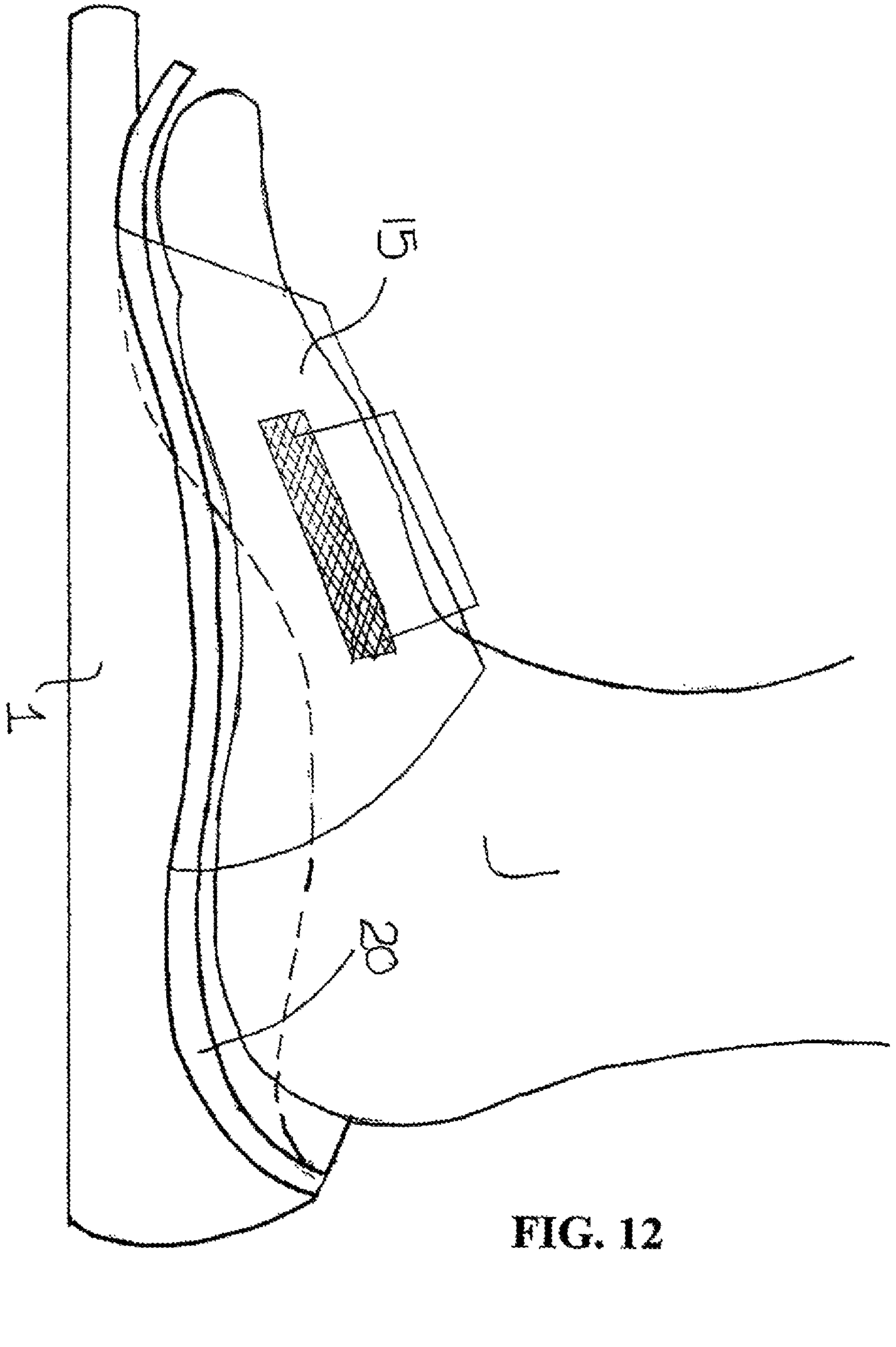
FIG. 12 is a side view of a right hand foot showing the foot wrap.

The lifted foot is then guided by the hands of the practitioner and placed back on the heated template 20 on the appropriate foot foam 1 so the foot is on top of the heated blank orthotic 20 on the foot foam 1. This is then wrapped about the sole of the foot by means of a wrap 15, which had been placed in advance between the foam 1 and the template 20, to conform the heated orthotic template 20 to the foot. This is shown in FIGS. 11 and 12 and prevents drooping or draping of the orthotic 20 away from the foot, and particularly the sides.

The wrap 15 is positioned on top of the foot foam 1 before the template is placed in position. That is, the template sits on top of the wrap.

In another embodiment, the wrap 15 can be integrally formed with the foot foam 1 but it must be remembered then that the foam 1 would need to be moved with the foot and orthotic 20 into the Windlass position (as below) for the orthotic 20 to be allowed to set.

The foot wrap 15 can be integrally formed as part of the foot foam supports 1, or could be a separate element that is simply wrapped around the foot and the heated orthotic template 20. The wrap 15 is composed of any type of elasticised or stretchable fabric or mesh. The wrap 15 may be secured by means of Velcro or buttons or studs, ties or the like.

Once the heated blank orthotic 20 is wrapped around the foot of the patient, the cuboid support 12 is disposed on the outside of the foot or the foot is placed over a cuboid bladder 7 or the like when such devices are used.

The cuboid support 12 is then pushed upwardly by the practitioner until resistance is felt and preferably more force is applied until the foot starts to move, raising the lateral arch cuboid area of the foot via vertical, translation and/or rotational forces until the foot either is moved into a neutral position or cannot be moved any further towards neutral position or has reached its end range of motion. It will be appreciated that in the case of a patient with a pronated foot, the movement of the cuboid curve will be modest relative to the extent of movement created by use of the MLA curve.

The medial longitudinal arch support 11 is then disposed under the arch of the foot or the foot is placed over a MLA bladder 8 or the like (eg support 11 and 12) when such devices are used and this is pushed upwardly by the practitioner until resistance is felt and preferably more force is applied until the foot starts to move, raising the arch via vertical, translation and rotational forces until the foot either is moved into a neutral position or cannot be moved any further towards neutral position or has reached its end range of motion.

As noted above, the patient may instead be standing on a bladder 8 and this is simply pumped up or otherwise moved to have the same effect.

Optionally, the practitioner may ask the patient to roll their ankle, inwardly or outwardly as required, thereby assisting in the movement of the foot via the cuboid curve 11 or MLA curve 12 to its optimal corrected position.

In the case where a bladder 7 & 8 or the like device is not being used, once the MLA and cuboid supports 11 & 12 are moved into position a wedge or other supporting/packing material (not illustrated) is inserted under the cuboid and the arch to maintain the foot in a corrected position and stop the areas corrected by supports 11 & 12 from moving. The supports 11 & 12 are maintained between the packing material and foam 1 retaining the orthotic 20 in the corrected position.

When the arch and cuboid of the foot have been adjusted so the foot is in a more neutral position, the rear foot alignment curve 201 may be adjusted to correct any mis-alignment through the calcaneus (heel) with the same principles applying in the correction process. Further, the width of the patient's stance may be narrowed to approximately hip width by adjusting actuator 116 shown in FIG. 1.

Figure 14:
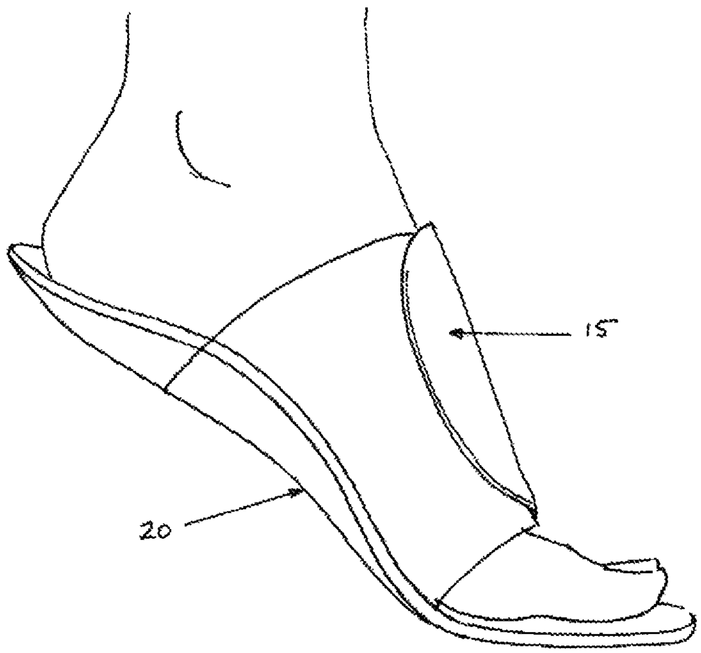
FIG. 14 is a side view of a foot with toes in dorsiflexed position.
Figure 15:
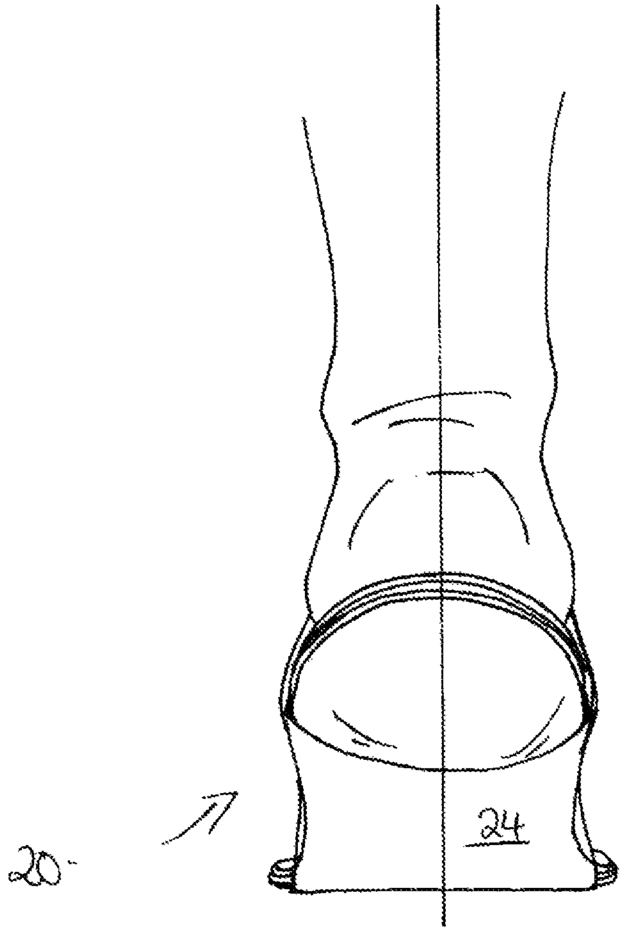
FIG. 15 is a schematic end view of the foot of FIG. 14.

With the foot in the corrected position, the patient then lifts one of their heels (FIGS. 14 & 15 in side and rear view) and places their weight on the front of their foot, most preferably substantially on the big toe with their toes dorsiflexed and the knee in flexion, positioned over the centre of the foot. This establishes the Windlass Mechanism which is the winding of the plantar fascia and it is this mechanism which stabilizes the foot when walking. This centres the talus bone by stabilising the sub-talar joint. In other words, movement to establish the Windlass mechanism allows the true arch shape to be obtained by winding the plantar fascia from metatarsals 1 to 5 but particularly the first metatarsal and the arch is then in its 'least straightened position' or maximum achievable arch height.

At this stage, all of the exposed underside material of the orthotic 20, proximal to the metatarsals through the midfoot and heel areas, is cooled down by applying a cool temperature source. This is most preferably an aerosol freeze spray such as commonly used by athletes such as VITALIC® Instant Ice Sports Spray (see https://www.airssential.com.au/productdetails.aspx?prdid=37), or CRC® or AEROSOLVE® brand aerosol can freeze sprays. These work by the evaporation of butane or propane, for example.

Saturation of the wrap may be required to ensure sufficient cooling of the orthotic through the midfoot.

Any alternate preferred means can be used such as cooled or frozen gel pack, and the foot wrap 15 may include a pouch or pocket (not illustrated) to allow insertion of a gel pack. Such cooling means may be integrated into the foot foam supports 1 or the support surfaces 2. For example, leaving channels in the foot foams 1 terminating at the surface and that are connectable to a freeze spray or cooling source so that the cooling is done from below by an integral source.

The foot is then raised to clear the foot foam 1. The foot wrap 15 is then released. It will be appreciated that in some Figs the orthotic 20, orthotic top cover 21 and foot wrap 15 are omitted in order to clearly illustrate the position of the foot.

The foot wrap 15 is preferably perforated such as 2 mm thick neoprene formed from an elastic woven material. This is to allow air or other cooling materials (gas or even liquid) to freely pass through it to more efficiently cool the formed orthotic 20.

At this stage, the orthotic 20 is removed to a freezer or otherwise cooled to well below the softening point but can be slightly reshaped if desired before completely cooling. An orthotic 20 of the preferred embodiment is shown in FIG. 16 in the finished form to be disposed in a shoe to correct the position of the foot. As noted by the nature of thermoplastic upper and lower materials, they can be reheated so substantive reshaping can occur if necessary. The orthotic 20 on the other foot is then cooled, removed and treated in the same manner.

The orthotic 20 can advantageously be later re-heated in specific areas to deflect or re-shape the orthotic 20 as desired.

After an orthotic for a patient standing in a corrected stance is formed, a region about the arch on the bottom of the cooled orthotic may be 'stiffened' or 'stabilised' so as to resist downward forces applied by the foot onto the orthotic. This is preferably done by attaching a suitably dimensioned volume of foam, ethyl vinyl acetate or other material (an example is shown at element 25 in FIG. 16C) over the region or filling it with an expanding foam or gel. Excess material is then ground or cut away.

Figure 17:
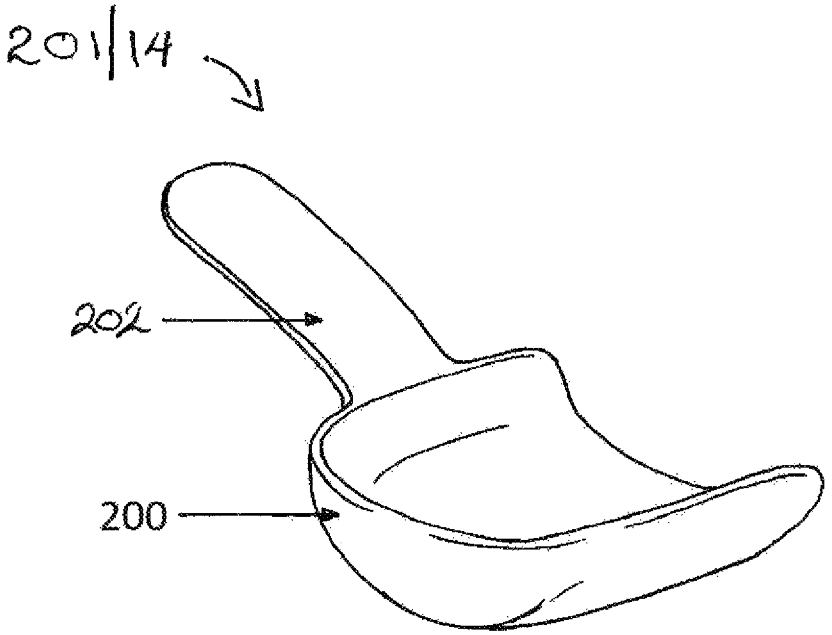
FIG. 17 is a perspective view of an alternative a left foot heel support according to another preferred embodiment for use in making orthotics according to another preferred embodiment.

Referring to FIG. 17, there is shown a heel support 200 according to another preferred embodiment. It will be appreciated that the heel support 200 of this embodiment is similar to the rear and fore foot curves 14 and 14' respectively. In this embodiment, the pillars 108 are not used and the heel support 200 is manually operated. Here, components 203-210 as shown in FIG. 2 are removed. An alternate arm 202 is attached to the heel support 201 and this sits at an angle of between 30° and 60° to horizontal to permit rotation of the heel support in a manner substantially equivalent to that achieved by use of components 203-210. This movement could also be achieved without having an arm 202 extending from the outside of the support 200, where the practitioner could apply downward force to the outside or the inside of the curve to push on the inside or the outside of the plantar heel area. Rear and fore foot curves 14 and 14' are functionally similar to support 200 without a handle 202.

Figure 19:
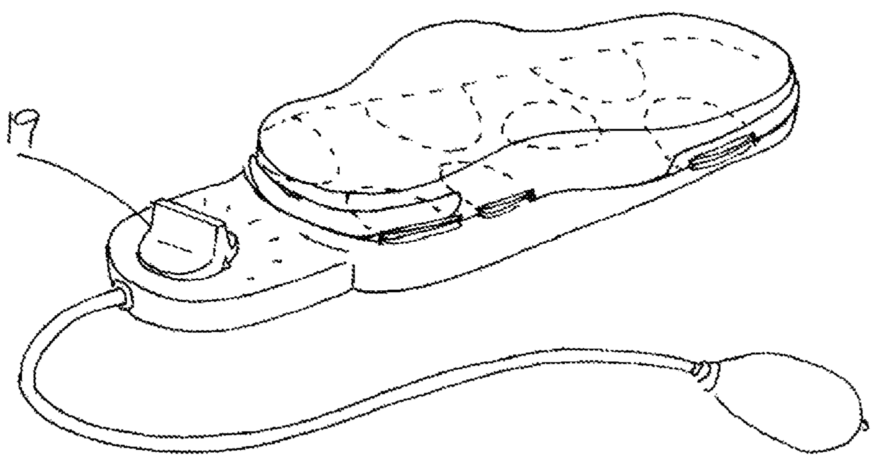

Turning to FIGS. 18 & 19, there is shown another preferred embodiment in which the means of directing air into the bladders 7 and 8 may alternately consist of a single hand pump linked to a valve mechanism 19. This valve mechanism 19 can be altered so as to selectively direct the air into each individual bladder 7 and 8 as desired. It will be appreciated that this is potentially more user friendly so far as only a single air-bulb or pump is required. In this embodiment, additional bladder 8D is provided to be disposed near or about the ball of the foot for vertical movement thereof.

Particularly, bladder 8D is intended to be located proximal to the metatarsals. This bladder is intended to create "a dome effect" and provide a convex bulge in the orthotic so as to provide additional support to this area of the plantar surface of the foot. It can be seen that the foot foam 1 sits on support surface 6 having the valve mechanism 19 and bladders 7 & 8 integrated therewith. Further, it can be seen that rear foot curve 14 is employed together with fore foot curve 14'.

Figure 20:
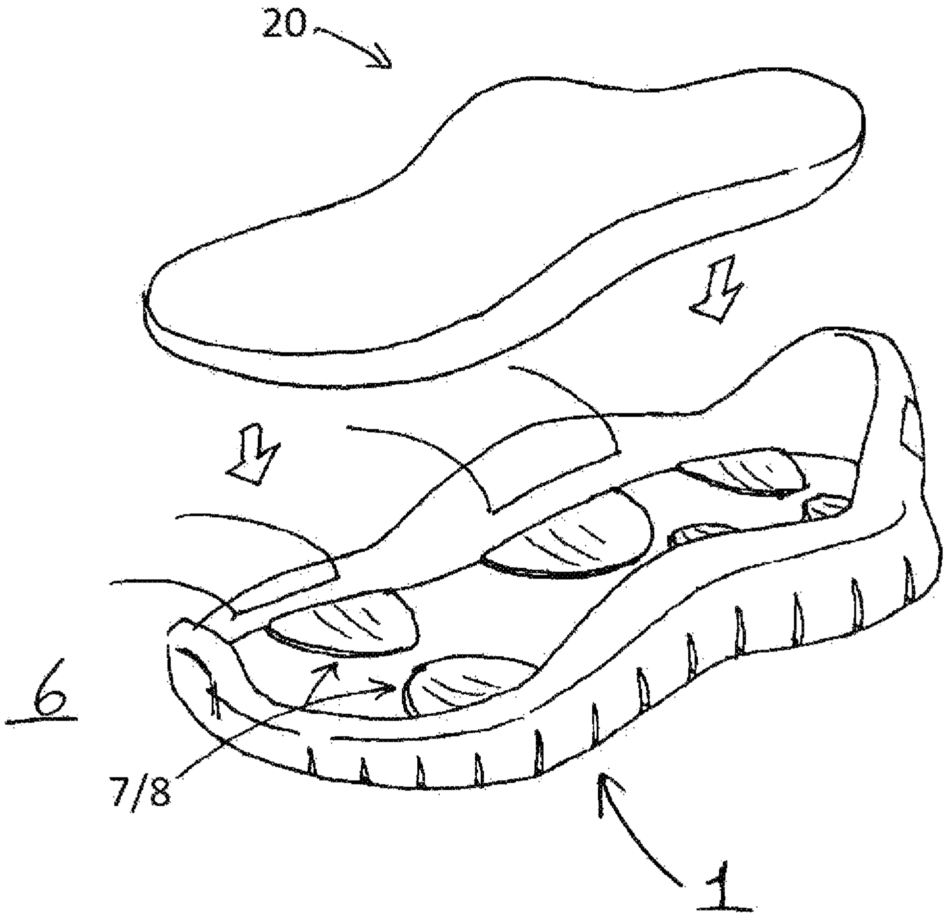
FIGS. 20 & 21 is an exploded part perspective view and an assembled perspective of an alternative support platform in the form of a shoe for use in making a foot orthotic according to the preferred embodiment.
Figure 21:
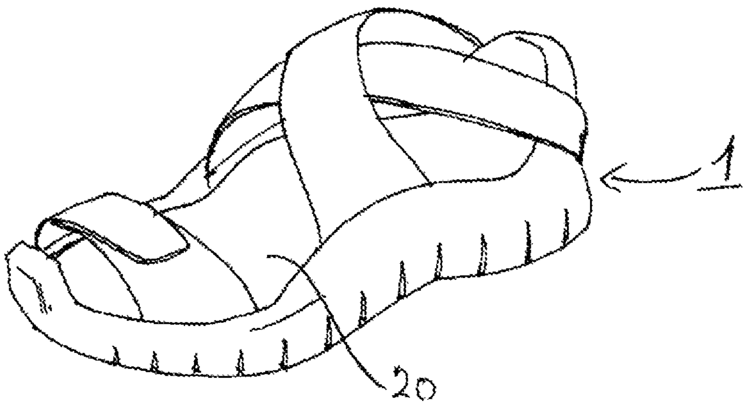

In respect of FIGS. 20 & 21, the foot foam 1 again sits on a support surface 6 similarly to FIGS. 18 & 19. However, the foot foam 1 sits atop platform 6 and when the patient stands on foot foam 1 with a heated orthotic 20 disposed intermediate, the support surface is wrapped about the patient's foot to retain the foot in position in a shoe-like manner. The valve mechanism 19 of FIGS. 18 & 19 can be employed and it will be appreciated that an actuator or pneumatic supply may be associated with the platform 6 in this embodiment and be worn around the waist of the patient and connected via a tube or hose or the like to the bladders, for example.

Figure 22:
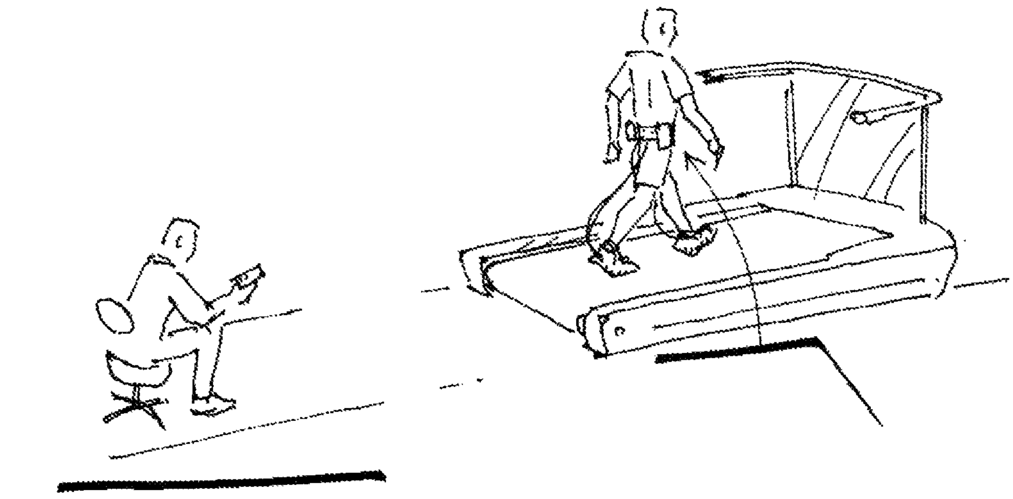
FIG. 22 is a perspective view of a patient wearing the support platform of FIGS. 20 & 21 whilst walking on a treadmill in front of a practitioner.

This is most advantageous as it allows the patient to actually walk once the heated orthotics are in place and initial corrections made. The practitioner can then observe any mis-alignment and make further adjustments accordingly. For example, the practitioner can sit behind the patient whilst they are walking or running on a treadmill such as shown in FIG. 22 to provide a dynamic understanding of the adequacy of the correction. This can offer improved accuracy in correction for a patient as opposed to simply standing in the one spot. It will be appreciated that optical measurement equipment such as laser positioning can be used to augment the practitioner's view of the movement and positioning of the patient.

Figure 23:
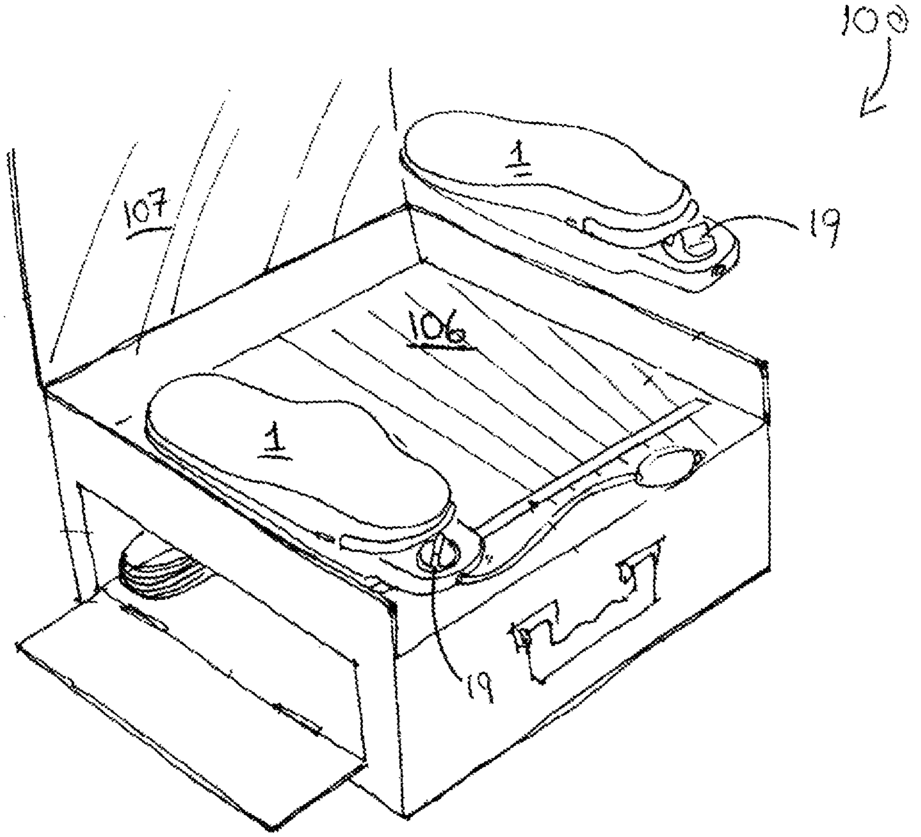
FIG. 23 is a perspective view of a portable support platform for use in making a foot orthotic according to the preferred embodiment.

Referring to FIG. 23, there is shown an alternative embodiment of the support platform 100 shown in FIG. 1 that is transportable. In this embodiment, pillars 108 and rear and fore-foot supports 200 & 300 respectively are not employed but a support platform similar to that shown in FIG. 4 is provided (although only one is shown in FIG. 23. Here, the support platform 106 is recessed from sidewalls so as to be able to receive mirror 107 folded on top to form a closed box. The foot foams 1 are able to be positioned relative to each other and to allow for a particular patient's stance and orientation in the horizontal plane. These are then fixed in position and the patient is able to stand on them. A sphygmomanometer air pump actuator is shown in this preferred embodiment for actuating the bladders.

Whilst the above preferred embodiments principally describe the use of orthotic 20 formed from two or more thermoplastic material layers 22 and 23 that may both be three-quarter length or one full-length and the other three-quarter length, this can be replaced by a single layer thermoplastic material having a graduated or differential thickness to replicate the response provided by thermoplastic material layers 22 and 23. In such an embodiment, the thickness is graduated from thickest at the heel to thinnest at the toe end, or it could change at specific intervals to compensate for increased loads or forces from particular areas of the foot when in use.

It will be appreciated that once an orthotic 20 is formed, it can be advantageous to provide some support material 25 to prevent the thermoplastic material deforming over time under load or when the orthotic becomes warmed. The support material is typically a relatively stiff foam that can be adhered to the underside of the orthotic 20 and then ground to an optimal shape to be received in a shoe. It will be appreciated that a gel, expandable foam, epoxy resin or other two-part mixture, or rubber filler, for example, may be employed to serve this purpose.

The foregoing describes only some preferred embodiments of the present invention and modifications, obvious to those skilled in the orthotic arts, can be made thereto without departing from the scope of the present invention.

The term "comprising" (and its grammatical variations) as used herein is used in the inclusive sense of "including" or "having" and not in the exclusive sense of "consisting only of".

The invention claimed is:

1. A method of providing a blank foot orthotic for use in forming a castless orthotic for a patient's foot in need thereof, the method comprising the steps of:

- preparing an orthotic template for the foot wherein the template extends between a heel end and a toe end;
- attaching full length upper thermoplastic material to a three-quarter length lower thermoplastic material; and
- attaching an outer lower layer to the lower thermoplastic material and attaching an outer upper layer to the upper thermoplastic material.

2. A method according to claim 1 wherein the full length upper and three quarter length lower thermoplastic materials are substantially planar.

3. A method according to claim 1 wherein the lower thermoplastic material is glued to the upper thermoplastic material, or the two are melted together.

4. A method according to claim 1 wherein the outer lower layer attached to the lower thermoplastic material is a woven or non-woven fabric.

5. A method according to claim 1 wherein the full length thermoplastic upper thermoplastic material is thicker or of equal thickness to the three quarter length thermoplastic lower material.

6. A method according to claim 5 wherein the lower three quarter thermoplastic lower material is about 1.2 mm thick and the upper thermoplastic material is about 1.4 mm thick.

7. A method according to claim 1 wherein the outer lower layer attached to the lower thermoplastic material is a woven or non-woven fabric adhered to the lower thermoplastic material.

8. A method according to claim 7 wherein the outer lower layer is glued to the lower thermoplastic sheet material.

9. A method according to claim 1 wherein upper and lower thermoplastic materials are configured to be softened by heating thereof at a temperature of 80° to 100° C.

10. A method according to claim 1 wherein the upper and lower thermoplastic materials are composed of a polycaprolactone.

11. A method according to claim 1 including the step of adhering a lower fabric or sheet layer to the lower thermoplastic material.

12. A method according to claim 1 including the step of adhering a top foam or cushion layer to the upper thermoplastic material.

13. A method according to claim 12 wherein the top foam or cushion layer is formed from leather, vinyl, ethylvinylacetate (EVA) or neoprene.

14. A method according to claim 1 including the step of configuring the outer lower layer to have a stiffening support material adhered thereto.

15. A blank foot orthotic comprising:

- a template for the foot extending between a heel end and a toe end;
  - a full length upper thermoplastic material attached to a three-quarter length lower thermoplastic;
  - an outer lower layer attached to the lower thermoplastic material and an outer upper layer attached to the upper thermoplastic.

16. A blank foot orthotic according to claim 15 wherein the full length upper and three quarter length lower thermoplastic materials are substantially planar.

17. A blank foot orthotic according to claim 15 wherein the lower thermoplastic material is glued to the upper thermoplastic material, or the two are melted together.

18. A blank foot orthotic according to claim 15 wherein the outer lower layer attached to the lower thermoplastic material is a woven or non-woven fabric.

19. A blank foot orthotic according to claim 15 wherein the full length thermoplastic upper thermoplastic material is thicker or of equal thickness to the three quarter length thermoplastic lower material.

20. A blank foot orthotic according to claim 19 wherein the lower three quarter thermoplastic lower material is about 1.2 mm thick and the upper thermoplastic material is about 1.4 mm thick.

21. A blank foot orthotic according to claim 15 wherein the outer lower layer attached to the lower thermoplastic material is a woven or non-woven fabric adhered to the lower thermoplastic material.

22. A blank foot orthotic according to claim 15 wherein upper and lower thermoplastic materials are configured to be softened by heating thereof at a temperature of 80° to 100° C.

23. A blank foot orthotic according to claim 15 wherein the upper and lower thermoplastic materials are composed of a polycaprolacetone.

24. A blank foot orthotic according claim 15 including the step of configuring the outer lower layer to have a stiffening support material adhered thereto.

* * * * *